United States Patent

Loomis et al.

Patent Number: 6,027,496
Date of Patent: Feb. 22, 2000

[54] REMOVAL OF STRATUM CORNEUM BY MEANS OF LIGHT

[75] Inventors: Neil W. Loomis, Racine, Wis.; Peter M. Bojan, Grayslake, Ill.; Timothy P. Henning, Vernon Hills, Ill.; Mark R. Pope, Grayslake, Ill.; Andrew J. Muetterties, Mundelein, Ill.

[73] Assignee: Abbott Laboratories, Abbott Park, Ill.

[21] Appl. No.: 08/823,940

[22] Filed: Mar. 25, 1997

[51] Int. Cl.⁷ .................................................. A61B 17/36
[52] U.S. Cl. ................................. 606/9; 606/11; 607/89
[58] Field of Search .................................. 606/2–3, 9–12

[56] References Cited

U.S. PATENT DOCUMENTS

| | | |
|---|---|---|
| 4,622,971 | 11/1986 | Yamamoto et al. |
| 4,775,361 | 10/1988 | Jacques et al. |
| 4,939,336 | 7/1990 | Meyer et al. |
| 5,165,418 | 11/1992 | Tankovich . |
| 5,290,273 | 3/1994 | Tan ................................................ 606/9 |
| 5,423,803 | 6/1995 | Tankovich et al. |
| 5,458,140 | 10/1995 | Eppstein et al. |
| 5,554,153 | 9/1996 | Costello et al. ............................ 606/9 |
| 5,599,342 | 2/1997 | Hsia et al. .................................. 606/9 |
| 5,628,744 | 5/1997 | Coleman et al. ......................... 606/12 |
| 5,643,252 | 7/1997 | Waner et al. ............................... 606/9 |
| 5,658,323 | 8/1997 | Miller ....................................... 607/89 |

FOREIGN PATENT DOCUMENTS

| | | |
|---|---|---|
| 0312650 | 4/1989 | European Pat. Off. . |
| 3245846 | 7/1983 | Germany . |
| 4314428 | 11/1992 | Japan . |
| 9409713 | 5/1994 | WIPO . |
| 9707734 | 3/1997 | WIPO . |

OTHER PUBLICATIONS

Goldsmith, Physiology, Biochemistry, and Molecular Biology of Skin, Oxford University Press (1991), chapters 1–2.

Primary Examiner—Michael Peffley
Assistant Examiner—Roy Gibson
Attorney, Agent, or Firm—David L. Weinstein

[57] ABSTRACT

A method for increasing the permeability of the stratum corneum by means of a source of light, preferably a laser, more preferably a pulsed laser. By increasing the permeability of the stratum corneum, access to the interstitial fluid is achieved, thereby enabling measurement of analytes in the interstitial fluid. In one aspect, the method comprises the steps of:

(a) providing a source of light having a wavelength of from about 930 nm to about 1040 nm; and (b) exposing a region of the stratum corneum of the patient to said source of light for a period of time sufficient to form an opening in the stratum corneum.

Preferably, exposure of the region of the stratum corneum to the source of light is ceased when an amount of interstitial fluid fills the opening in the stratum corneum, which amount is sufficient to cause the scatter intensity of the light reflected from the surface of the interstitial fluid occupying the opening in the stratum corneum to differ from the scatter intensity of the light reflected from a region of the stratum corneum that is substantially free of interstitial fluid. The invention also involves an apparatus for carrying out the foregoing method.

22 Claims, 1 Drawing Sheet

REMOVAL OF STRATUM CORNEUM BY MEANS OF LIGHT

BACKGROUND OF THE INVENTION

1. Field of the Invention

This invention relates to a method and apparatus for forming an opening in the skin for the purpose of providing access to biological fluids for determining the concentration of analytes in the biological fluids.

2. Discussion of the Art

The prevalence of diabetes has been increasing markedly in the world. At this time, diagnosed diabetics represents about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

There are numerous devices currently available for diabetics to monitor the level of blood glucose. The best of these devices require the diabetic to prick a finger and to collect a drop of blood for placement on a strip, which is inserted into a monitor that determines the level of glucose in the blood. Pricking one's finger tends to be painful. Moreover, a relatively large wound is produced by the pricking device, typically a lancet or a needle. It is known that the pain arising from the finger prick deters diabetics from compliance with the monitoring regimen. Lack of compliance increases the risk of complications due to diabetes. Thus there is a need for a more painless and less traumatic means of collecting biological samples for monitoring one's level of glucose in blood.

Several patents have proposed that the level of glucose in blood can be monitored by measuring the level of glucose in interstitial fluid. In order to obtain samples of interstitial fluid, the barrier function of the stratum corneum must be overcome. Jacques, U.S. Pat. No. 4,775,361, discloses a method of ablating the stratum corneum of a region of the skin of a patient by using pulsed laser light of a wavelength, pulse length, pulse energy, pulse number, and pulse repetition rate sufficient to ablate the stratum corneum without significantly damaging the underlying epidermis. This patent discloses the use of laser light having a wavelength of 193 nm or 2940 nm. Laser light having wavelengths of 193 nm or 2940 nm can be provided by an excimer or Er:YAG light source, respectively, both of which are extremely expensive.

Tankovich, U.S. Pat. No. 5,423,803, discloses a process for the removal of superficial epidermal skin cells in the human skin. A contaminant having a high absorption in at least one wavelength of light is topically applied to the surface of the skin. Some of the contaminant is forced to infiltrate into spaces between superficial epidermal cells. The skin section is illuminated with short laser pulses at the above wave-length, with at least one of the pulses having sufficient energy to cause some of the particles to explode tearing off the superficial epidermal cells. In a preferred embodiment, the contaminant includes 1 micron graphite particles and the laser used in a Nd:YAG laser.

Zahrov, WO 94/09713, discloses a method for perforating skin comprising the steps of (a) focusing a laser beam in the shape of an ellipse at the surface of the skin with sufficient energy density to create a hole at least as deep as the keratin layer and at most as deep as the capillary layer; and (b) creating at least one hole, each hole having a width between 0.05 and 0.5 mm and a length of equal to or less than 2.5 mm. This patent discloses a variety of lasers suitable for carrying out this method. However, the method disclosed in Zahrov is limited to light source having a wavelength of 2940 nm. As stated previously, laser light of this wavelength can be provided by a Er:YAG light source, which is very expensive. Moreover, such a light source is relatively large, with the result that it would not be practical for use in a hand-held device.

It would be desirable to provide a method for providing an opening in the surface of the skin wherein an inexpensive light source is utilized, wherein the light source is of a size small enough to be portable and holdable in the hand of the user.

SUMMARY OF THE INVENTION

In one aspect, this invention provides a method for increasing the permeability of the stratum corneum by means of a source of light, preferably a laser, more preferably a pulsed laser. By increasing the permeability of the stratum corneum, access to the interstitial fluid is achieved, thereby enabling measurement of analytes in the interstitial fluid. The method comprises the steps of:

(a) providing a source of light having a wavelength of from about 930nm to about 1040 nm, preferably from about 950 nm to about 1010 nm, more preferably from about 970 nm to about 990 nm; and (b) exposing a region of the stratum corneum of the patient to said source of light for a period of time sufficient to form an opening in the stratum corneum.

Preferably, exposure of the region of the stratum corneum to the source of light is ceased when an amount of interstitial fluid fills the opening in the stratum corneum, which amount is sufficient to cause the scatter intensity of the light reflected from the surface of the interstitial fluid occupying the opening in the stratum corneum to differ from the scatter intensity of the light reflected from a region of the stratum corneum that is substantially free of interstitial fluid.

The wavelength at which the source of light is set is most preferably about 980nm. A source of light set at a wavelength of about 980 nm does not require the use of energy absorbing dyes, because a naturally occurring water band in the human body occurs at 980 nm. The source of light is preferably a laser, more preferably a pulsed laser.

In a preferred embodiment, an elliptical region of the stratum corneum is illuminated, the light source being a pulsed laser directed at the stratum corneum at an incident angle of from about 18° to about 32°, as measured from the surface of the stratum corneum to the source of light. The scatter intensity is observed by a broadband detector. As the stratum corneum is being removed, the opening in the skin in the region where the stratum corneum is removed will become filled with interstitial fluid, thereby changing the scatter intensity of reflected radiation. When the scatter intensity of light reflected from the surface of interstitial fluid occupying the opening formed in the stratum corneum measured after a given pulse of the laser (i. e., the nth pulse where n≧2) differs from the scatter intensity of light reflected from the stratum corneum measured after the first pulse of the laser (i. e., n=1) by approximately 5% to 10% or greater, the laser is turned off to prevent damage to the tissue underlying the stratum corneum.

In another aspect, this invention provides an apparatus capable of carrying out the above-described method. The apparatus comprises:

(a) a source of light, preferably a pulsed laser, for providing energy to form an opening in the stratum corneum;

(b) a lens assembly for collimating and focusing light from the source of light onto the surface of the stratum corneum;

(c) a broadband detector for detecting a signal related to the intensity of light reflected from the surface of the stratum corneum and from interstitial fluid that fills the opening formed in the stratum corneum by the collimated, focused light from the source of light;

(d) an amplifier for increasing the signal detected by the broadband detector;

(e) a sample and hold circuit for holding the first incremental signal received from the amplifier, preferably the first incremental signal resulting from the first pulse generated from a pulsed laser;

(f) a threshold comparator for comparing (1) an incremental signal received from the amplifier subsequent to the first incremental signal with (2) the first incremental signal received from the amplifier, preferably comparing the incremental signal measured after a given pulse generated from a pulsed laser with the signal measured after the first pulse generated from a pulsed laser;

(g) a signal generator and power control circuit for generating a signal to cause a laser driver circuit to drive current needed to operate the source of light at a desired power level; and (h) a means for commanding the signal generator to generate a signal;

(i) a means for commanding the sample and hold circuit to hold the first incremental signal received from amplifier;

(j) a means for commanding the threshold comparator to compare (1) an incremental signal received from the amplifier subsequent to the first incremental signal with (2) the first incremental signal received from the amplifier; and (k) a means for resetting the threshold comparator.

It is preferred that the signal generator (g) be a pulse generator. It is preferred that the means (h) for commanding the signal generator, the means (i) for commanding the sample and hold circuit, the means (j) for commanding the threshold comparator, and the means (k) for resetting the threshold comparator be a microcontroller, more preferably the same microcontroller for means (h), means (i), means (j), and means (k).

The present invention provides access to interstitial body fluid in a less painful and less time-consuming manner than does tape stripping and does not require the use of energy absorbing dyes that are required with light sources that provide light having wavelengths of 810 nm or 1064 nm.

DETAILED DESCRIPTION

Figure 1:
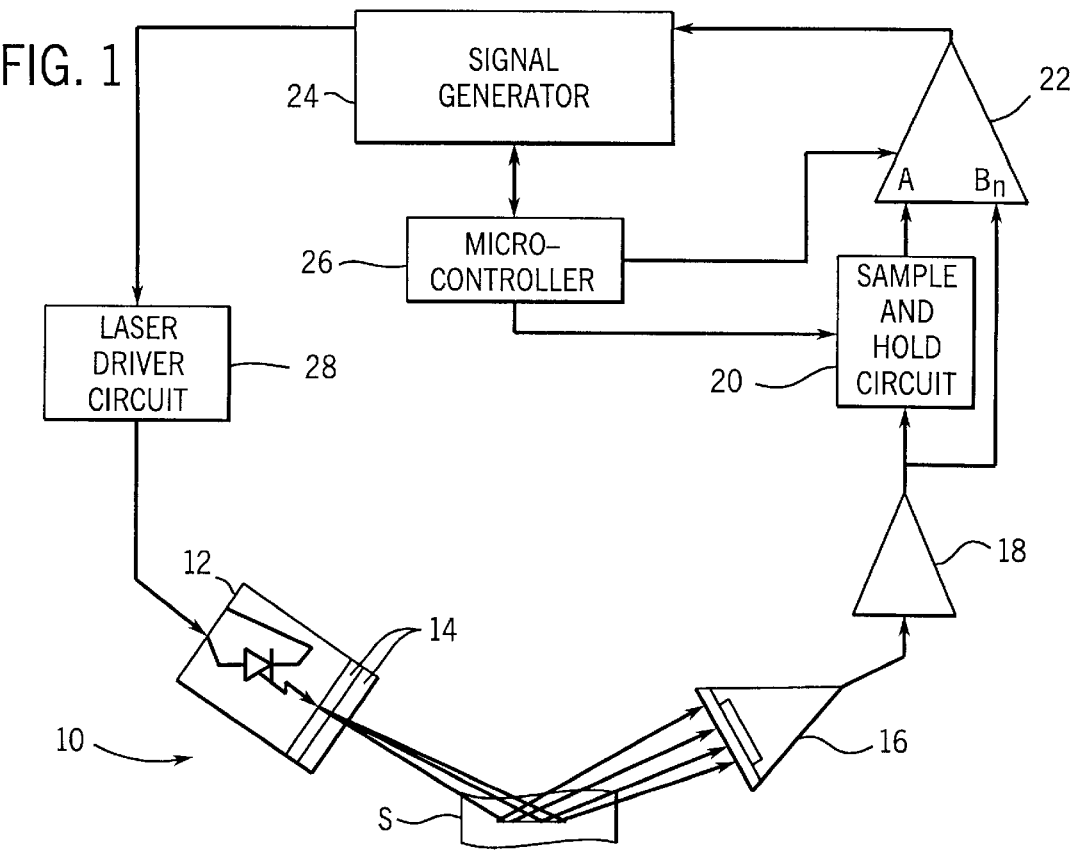
FIG. 1 is a schematic view of an apparatus suitable for carrying out the method of this invention.
Figure 2:
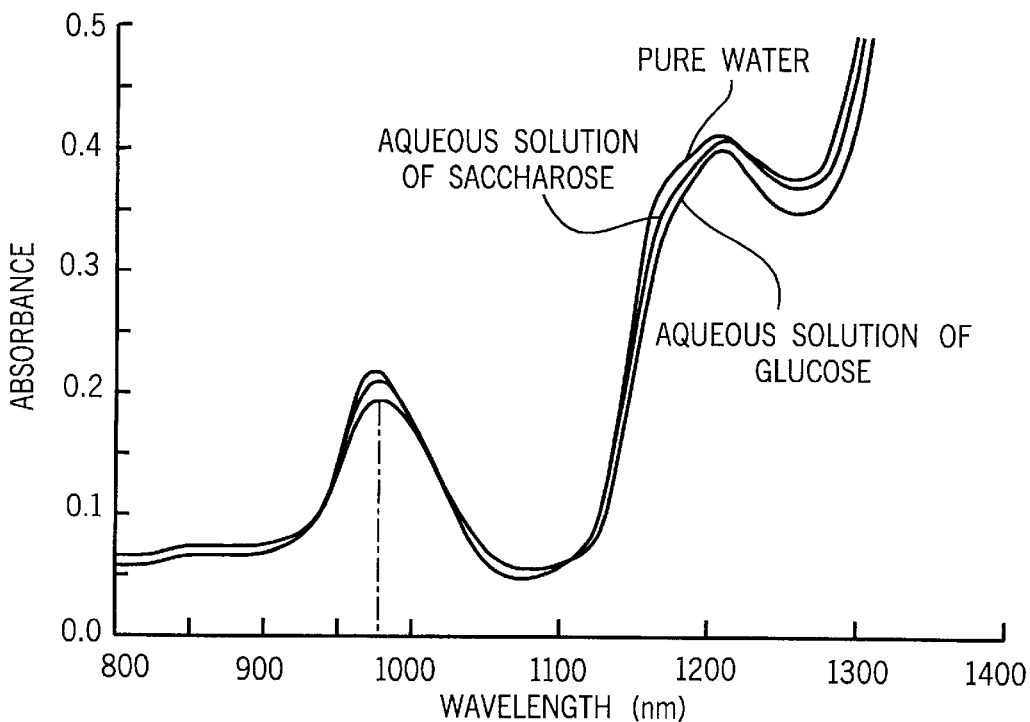
FIG. 2 is a graph illustrating water absorbance of the stratum corneum as a function of wavelength of light.

Referring now to FIG. 1, an apparatus 10 suitable for carrying out the method of this invention comprises a source of light 12, preferably a laser, and a lens assembly 14 for collimating and focusing light from source of light 12 onto the surface of the stratum corneum. The source of light 12 provides light at a wavelength of about 980 nm. As shown in FIG. 2, water exhibits an absorption maximum at 980 nm. The maximum allowable range for the light having a wavelength of 980 nm is from about 930 nm to about 1040 nm, preferably from about 950 nm to about 1010 nm, more preferably from about 970 nm to about 990 nm. If the tolerance is any wider, the absorbance peak is missed by so much that significantly more power is needed to remove the stratum corneum. The source of light 12 is preferably a diode laser. It is preferred that the laser be a low-cost solid state laser capable of delivering at least 250 mW of pulsed energy at the surface of the stratum corneum targeted at the 980 nm water absorption band and that the laser be sufficiently small to be portable and holdable in the hand of the user. Lasers suitable for the present invention include, but are not limited to, the OPC-A001-980-FC/100 laser, commercially available from Opto Power Corporation, Tucson, Ariz.

The lens assembly 14 comprises at least one lens. The number and arrangement of individual lenses for collimating and focusing is well-known to one of ordinary skill in the art.

The collimated, focused light from the source of light 12 strikes the stratum corneum of the skin of the patient. The stratum corneum is designated by the letter "S". The stratum corneum is described in detail in Goldsmith, *Physiology, Biochemistry and Molecular Biology of Skin*. Oxford University Press (1991), chapters 1 and 2, incorporated herein by reference. The light is focused so that it strikes the stratum corneum at a suitable incident angle.

A broadband detector 16 detects the scatter intensity of light reflected from the surface of the stratum corneum or from the surface of interstitial fluid contained in the opening formed in the stratum corneum. As used herein, the expression "scatter intensity" means the intensity of reflected and scattered infrared radiation coming from the irradiated region of the stratum corneum. The broadband detector 16 is preferably a germanium (Ge) detector, and the bandwidth typically ranges from 800 nm to 1700 nm. Broadband detectors suitable for this invention include, but are not limited to, those of the J16 series, commercially available from EG&G Corporation. These detectors are Judson's Germanium diodes.

The signal (typically a DC voltage) from the broadband detector 16 is amplified by an amplifier 18. The first incremental amplified signal from the amplifier 18 is sent to a sample and hold circuit 20. The second and subsequent amplified signals from the amplifier 18 are sent to a threshold comparator 22.

The sample and hold circuit 20 holds the first incremental signal (typically a DC voltage) received from the amplifier 18. The first incremental signal results from the first increment of light generated, preferably the first pulse of light generated from a pulsed laser. This signal is proportional to the infrared scatter intensity detected by the broadband detector 16 and amplified by the amplifier 18.

The threshold comparator 22 compares a given input signal, e. g., B, with a reference input signal, e. g., A. The reference input signal A has an adjustable threshold, which is set at a level above the noise level of the system. When the given input signal B differs from the reference input signal A by at least a set amount, i. e., the threshold, the output signal of the threshold comparator 22 generates a level transition or pulse. The level transition output signal from the threshold comparator 22 commands a signal generator 24 to stop any further signals from being generated until a microcontroller 26 resets the threshold comparator 22. The threshold comparator 22 is adjustable by a variable resistor. When the given input signal B does not differ from the reference input signal A by the threshold, the signal generator 24 continues to generate signals.

The cut-off, or set amount by which a given input signal B differs from the reference input signal A, is determined from the scatter intensity expected and is arbitrary. The cut-off is initially set to trigger the threshold comparator 22 when the scatter intensity of the nth increment of light energy (where $n \geq 2$) differs from the scatter intensity of the first increment of light energy (where n=1) by a specified percentage, typically 5% to 10% or greater. Increments of light energy are preferably delivered as pulses. However, other forms of delivery are also contemplated in this invention. A cut-off of at least about 5%, at least about 10%, at least about 15%, or at least about 20% is typically selected because noise level of the system could be as high as 5%, and the triggering level should be set sufficiently high above the noise level to prevent a premature cut-off before interstitial fluid begins to fill the opening created by the source of light.

The signal generator 24 generates signals upon commands given by the microcontroller 26. The signals from the signal generator 24 are sent to a source of light driver circuit 28. The signal generator 24 also includes a power control circuit to condition the signals for the source of light driver circuit 28. The source of light driver circuit 28 provides the drive currents required to operate the source of light 12 at the desired power level. It is preferred that the signal generator 24 be a pulse generator that generates pulses as the form of signal. Alternatively, the signal generator 24 can be a function generator. The microcontroller 26 generates the master timing and controls all programmed operations. The microcontroller 26 also resets the threshold comparator 22 and commands the sample and hold circuit 20 to hold the first incremental signal received from the amplifier 18.

Although microcontroller 26 is shown as a single component, which is responsible for commanding the signal generator to generate a signal, for commanding the sample and hold circuit to hold the first incremental signal received from amplifier, and for commanding the threshold comparator to compare (1) an incremental signal produced from the source of light subsequent to the first incremental signal with (2) the first incremental signal produced from the source of light, each of the foregoing functions can be carried out by a separate component, or, in the alternative, two or more of the foregoing functions can be carried out by an individual component.

All of the components described herein are commercially available, and proper selection thereof would not require undue experimentation by one of ordinary skill in the art.

The region illuminated by the source of light and lens assembly can be of any shape. An elliptical shape is preferred for the reasons that elliptically shaped wounds heal faster than circular wounds having a similar diameter and elliptical beams are more natural to conventional laser constructions.

An incident angle ($\alpha$) of 18° to 32° (25°±7°) from the plane of the skin is considered to be optimal for the angle of incoming radiation where the radiation scatter angle appears to peak between 20° and 46° ($\beta$) from the plane of the skin. The optimality of the signal is based on the optimal absorption of energy by the surface of the skin. On a smooth surface, the angle of incidence would be substantially equal to the angle of reflection. On a textured surface, such as the skin, irregularities cause the angle of reflection to vary from the angle of incidence.

It is possible to use a continuous wave laser instead of a pulsed laser. However, a continuous wave laser requires more power per unit time so the battery must be larger, consequently making the apparatus larger.

OPERATION

In order to carry out the method of this invention, the apparatus shown in FIG. 1 is provided. The apparatus of FIG. 1 is then positioned so that the source of light can be focused at a site on the body suitable for forming an opening in the stratum corneum and, preferably, from which opening biological fluid can be obtained, and, more preferably, collected for analysis. Then, the microcontroller 26 is switched on.

In the case of a pulsed laser, which is employed in the preferred embodiment, the signal generator 24 generates a pulse which is transmitted the laser driver circuit 28. The laser driver circuit 28 causes the laser 12 to emit a first pulse of light of from about 930 nm to about 1040 nm, preferably from about 950 nm to about 1010 nm, more preferably from about 970 nm to about 990 nm, most preferably at 980 nm. The lens assembly 14 collimates and focuses the pulse of light on the region of the stratum corneum where the opening is desired. The intensity of the reflected and scattered infrared radiation from the irradiated region of the stratum corneum is detected by the broadband detector 16. The detected signal from the broadband detector 16 is amplified by the amplifier 18 and stored in the sample and hold circuit 20. The value of the stored signal is the reference input signal A.

The microcontroller 26, the signal generator 24, the laser driver circuit 28, the laser 12, the lens assembly 14, the broadband detector 16, and the amplifier 18 operate in the same manner for each subsequent pulse of light generated. Each of these pulses of light, i. e., the given input signals, may be designated as given input signals $B_n$ where n represents the pulse number of the pulse of light generated from the source of light 12, beginning with n=1. For each pulse of light generated subsequent to the first pulse of light generated, the threshold comparator 22 compares the amplified input signal $B_n$ from the amplifier 18 with the reference input signal A. If the amplified input signal $B_n$ from the amplifier 18 does not differ from the reference input signal A by a set amount, i. e., the threshold, signals continue to be generated. If the amplified input signal $B_n$ from the amplifier 18 differs from the reference input signal A by a set amount, i. e., the threshold, the threshold comparator 22 provides a signal that causes the signal generator 24 to cease generating pulses, and, consequently, the laser ceases emitting light. The amplified input signal $B_n$ from the amplifier 18 will differ from the reference input signal A by a set amount when the intensity of the light scattered by the fluid that is filling the opening in the stratum corneum reaches the appropriate level. The appropriate level, as stated previously, is typically set so that the input signal differs from the reference input signal by at least about 5%, at least about 10%, at least about 15%, or at least about 20%, because noise level of the system could be as high as 5%, and the triggering level should be set sufficiently high above the noise level to prevent a premature cut-off before interstitial fluid begins to fill the opening created by the source of light. It is of course to be understood that the input signal $B_1$ is equal to the reference input signal A, and, consequently, the input signal $B_1$ cannot differ from the reference input signal A. After the signal generator 24 ceases generating pulses, the microcontroller 26 resets the threshold comparator 22.

The biological fluid rendered accessible by the formation of the opening in the stratum corneum can then be collected by conventional means, e. g., vacuum, and analyzed by conventional means, e. g., high pressure liquid chromatography, biosensors, reflectance strips.

The opening formed in the stratum corneum by the method or apparatus of this invention can also be used for the transdermal delivery of drugs, e. g., insulin, to a patient. In order to carry out such transdermal delivery of drugs, it is preferred that a transdermal drug delivery system comprising, for example, a reservoir containing the drug, be attached to the skin of the patient in such a manner that the drug can enter the opening formed by the method or apparatus of this invention. Means suitable for delivering the drug through the opening formed by the method or apparatus of this invention are well-known to those of ordinary skill in the art.

The present invention provides access to interstitial body fluid in a less painful and less time-consuming manner than does tape stripping and does not require the use of energy absorbing dyes that are required with light sources that provide light having wavelengths of 810 nm or 1064 nm.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for forming an opening in a region of the stratum corneum of a patient comprising the steps of:
    (a) providing a source of light having a wavelength of from about 930 nm to about 1040 nm; and
    (b) exposing said region of the stratum corneum of said patient to said source of light for a period of time sufficient to form an opening in the stratum corneum, wherein exposure of said region of the stratum corneum to said source of light is ceased when an amount of interstitial fluid occupies said opening in the stratum corneum, said amount of interstitial fluid having a surface that causes light from said source of light to scatter, said scattered light having a scatter intensity, said amount of interstitial fluid being sufficient to cause said scatter intensity of light reflected from said surface of said interstitial fluid occupying said opening in the stratum corneum to differ from the scatter intensity of light reflected from a region of the stratum corneum that is substantially free of interstitial fluid.

2. The method of claim 1, wherein said source of light provides a pulse of light that results in a scatter intensity and at least one pulse of light subsequent to said first pulse of light, each of said at least one pulse of light subsequent to said first pulse of light resulting in a scatter intensity.

3. The method of claim 2, wherein exposure is ceased when the scatter intensity resulting from a pulse of light provided subsequent to said first pulse of light differs from the scatter intensity resulting from said first pulse of light by at least about 5%.

4. The method of claim 2, wherein exposure is ceased when the scatter intensity resulting from a pulse of light provided subsequent to said first pulse of light differs from the scatter intensity resulting from said first pulse of light by at least about 10%.

5. The method of claim 2, wherein exposure is ceased when the scatter intensity resulting from a pulse of light provided subsequent to said first pulse of light differs from the scatter intensity resulting from said first pulse of light by at least about 20%.

6. The method of claim 1, wherein said region of the stratum corneum exposed to said source of light is elliptical in shape.

7. The method of claim 1, wherein said source of light exposes the stratum corneum at an angle of from about 18° to about 46°, as measured from said surface of the stratum corneum to said source of light.

8. The method of claim 1, wherein said source of light is a laser.

9. The method of claim 1, wherein said source of light is a pulsed laser.

10. The method of claim 1, further including the step of analyzing the interstitial fluid collected from said opening in the stratum corneum.

11. The method of claim 1, wherein said source of light has a wavelength of from about 950 nm to about 1010 nm.

12. The method of claim 1, wherein said source of light has a wavelength of from about 970 nm to about 990 nm.

13. A method for collecting interstitial fluid from an opening in a region of the stratum corneum of a patient comprising the steps of:
    (a) exposing said region of the stratum corneum of said patient to a source of light for a period of time sufficient to form an opening in the stratum corneum, wherein exposure of said region of the stratum corneum to said source of light is ceased when an amount of interstitial fluid occupies said opening in the stratum corneum, said amount of interstitial fluid having a surface that cause light from said source of light to scatter, said scatter light having a scatter intensity, said amount of interstitial fluid being sufficient to cause said scatter intensity of light reflected from said surface of said interstitial fluid occupying said opening in the stratum corneum to differ from the scatter intensity of light reflected from a region of the stratum corneum that is substantially free of interstitial fluid; and
    (b) collecting interstitial fluid from said opening in the stratum corneum.

14. The method of claim 13, wherein said source of light provides a pulse of light that results in a scatter intensity and at least one pulse of light subsequent to said first pulse of light, each of said at least one pulse of light subsequent to said first pulse of light resulting in a scatter intensity.

15. The method of claim 13, wherein exposure is ceased when the scatter intensity resulting from a pulse of light provided subsequent to said first pulse of light differs from the scatter intensity resulting from said first pulse of light by at least about 5%.

16. The method of claim 13, wherein exposure is ceased when the scatter intensity resulting from a pulse of light provided subsequent to said first pulse of light differs from the scatter intensity resulting from said first pulse of light by at least about 10%.

17. The method of claim 13, wherein exposure is ceased when the scatter intensity resulting from a pulse of light provided subsequent to said first pulse of light differs from the scatter intensity resulting from said first pulse of light by at least about 20%.

18. The method of claim 13, wherein said region of the stratum corneum exposed to said source of light is elliptical in shape.

19. The method of claim 13, wherein said source of light exposes the stratum corneum at an angle of from about 18° to about 46°, as measured from the surface of the stratum corneum to said source of light.

20. The method of claim 13, wherein said source of light is a laser.

21. The method of claim 13, wherein said source of light is a pulsed laser.

22. The method of claim 13, further including the step of analyzing the biological fluid collected from the stratum corneum.

* * * * *